(12) United States Patent
Evans

(10) Patent No.: US 7,350,536 B2
(45) Date of Patent: Apr. 1, 2008

(54) VACUUMIZED RECEPTACLE FOR SAMPLE COLLECTION

(75) Inventor: Robert W. Evans, Portland, OR (US)

(73) Assignee: Evans Components, Inc., Portland, OR (US)

( * ) Notice: Subject to any disclaimer, the term of this patent is extended or adjusted under 35 U.S.C. 154(b) by 0 days.

(21) Appl. No.: 11/249,962

(22) Filed: Oct. 14, 2005

(65) Prior Publication Data

US 2007/0084300 A1    Apr. 19, 2007

(51) Int. Cl.
F16K 1/14    (2006.01)
G01N 1/00   (2006.01)

(52) U.S. Cl. ............................ 137/315.17; 137/15.22; 73/863; 251/149

(58) Field of Classification Search ............... 73/863, 73/863.21, 863.23; 251/315.16, 315, 149; 137/15.22, 315.17
See application file for complete search history.

(56) References Cited

U.S. PATENT DOCUMENTS

| 3,267,558 | A | * | 8/1966 | Wilson .................. 29/890.127 |
| 3,618,393 | A |   | 11/1971 | Principe ................ 73/421.5 R |
| 3,847,552 | A | * | 11/1974 | Hobgood et al. ............. 436/28 |
| 3,938,367 | A | * | 2/1976 | Fletcher et al. .......... 73/863.22 |
| 4,040,299 | A |   | 8/1977 | Snyder .................. 73/421.5 R |
| 4,455,881 | A | * | 6/1984 | Clark et al. .............. 73/863.21 |
| 4,649,760 | A | * | 3/1987 | Wedding ................. 73/863.23 |
| 4,771,803 | A | * | 9/1988 | Berchem et al. ............ 137/375 |
| 4,795,133 | A | * | 1/1989 | Berchem et al. ............ 251/171 |
| 5,031,401 | A | * | 7/1991 | Hinderks ..................... 60/302 |
| 5,069,240 | A | * | 12/1991 | Kurkjian, Jr. ............ 137/15.22 |
| 5,174,959 | A | * | 12/1992 | Kundu et al. .................. 422/59 |
| 5,621,180 | A | * | 4/1997 | Simon et al. ............ 73/864.52 |
| 6,019,145 | A | * | 2/2000 | Savidge ....................... 141/38 |
| 6,073,648 | A | * | 6/2000 | Watson et al. ............. 137/375 |
| 6,263,744 | B1 | * | 7/2001 | Russell et al. ............. 73/865.5 |
| 6,865,926 | B2 | * | 3/2005 | O'Brien et al. ............ 73/23.27 |
| 2003/0141480 | A1 | * | 7/2003 | Green ................... 251/315.01 |

* cited by examiner

Primary Examiner—Hezron Williams
Assistant Examiner—Rodney Frank
(74) Attorney, Agent, or Firm—Black Lowe & Graham PLLC

(57) ABSTRACT

A portable receptacle is vacuumized for use in taking an air or gas sample for subsequent examination to determine type, origin, components of the air or gas. Critical to a long shelf life of the vacuumized receptacle is a valve which virtually seals the receptacle for months or years permitting storage of the receptacle in a state ready for immediate use at a site. The valve utilizes a positionable member plated with a noble metal. A filter serves to collect particulate from the air or gas flow into the receptacle. A funnel shaped collector aids in the collection.

19 Claims, 3 Drawing Sheets

VACUUMIZED RECEPTACLE FOR SAMPLE COLLECTION

BACKGROUND OF THE INVENTION

The present invention concerns a receptacle, normally in a vacuumized state, for the selective taking of gas or air samples for forensic evaluation.

In the investigation of events, such as explosions or accidents involving a gas, samples taken are helpful in determining cause and/or origin. The use of stored vacuumized receptacles opened at a site for the intake of ambient air or gas samples has been proposed but to be practical requires that sample taking must occur promptly after the event. In the instance of an explosion chemical analysis of a sample can help in the determination of the explosive type and origin. Similarly, the timely collection of any airborne particulate at a site may be helpful.

It would be desirable to have a number of vacuumized containers stored at selected sites to permit rapid delivery to a leak, spill or explosion site. Heretofore, the maintenance of a vacuumized state in stored containers has proved difficult in view of known valve designs permitting some leakage.

U.S. Pat. No. 3,618,393 discloses a vacuum tank with an inlet controlled by a manually operated valve.

U.S. Pat. No. 4,040,299 discloses a vacuum tank provided with a vacuum controlling valve and an inlet controlling second valve, a vacuum gauge and a filter located at the inlet end of a tubular inlet. A gas sample is drawn from a vacuum tank via a self-sealing septum, as is the case with many prior art vacuum receptacles.

U.S. Pat. No. 6,073,648 discloses a ball valve for use in highly corrosive and highly erosive environments. Wetted surfaces 24a of the valve body and wetted surface 28a of the ball component are firstly coated with a noble metal and secondly with a ceramic material, which per Col 3., Lines 58-63, is conceded to be porous and hence the patented valve does not address the problem solved by the present invention, i.e., sealing a vacuumized receptacle against atmospheric pressure over a period of several months and perhaps years.

SUMMARY OF THE PRESENT INVENTION

The present invention is based upon a vacuumized sample receptacle to maintain a vacuumized state over a period of months or longer until needed for sample taking. A valve component of the present receptacle has an external outermost coating of a noble metal contributes to a virtually perfect seal. Further, ambient gas or air entering the receptacle results in the deposit of airborne particulate on screen and fabric components of the receptacle.

The present receptacle provides an adequately sized inlet orifice for the insertion of a probe for retrieving any collected matter for analysis.

DETAILED DESCRIPTION OF THE PREFERRED EMBODIMENTS

Figures 1, 1A:
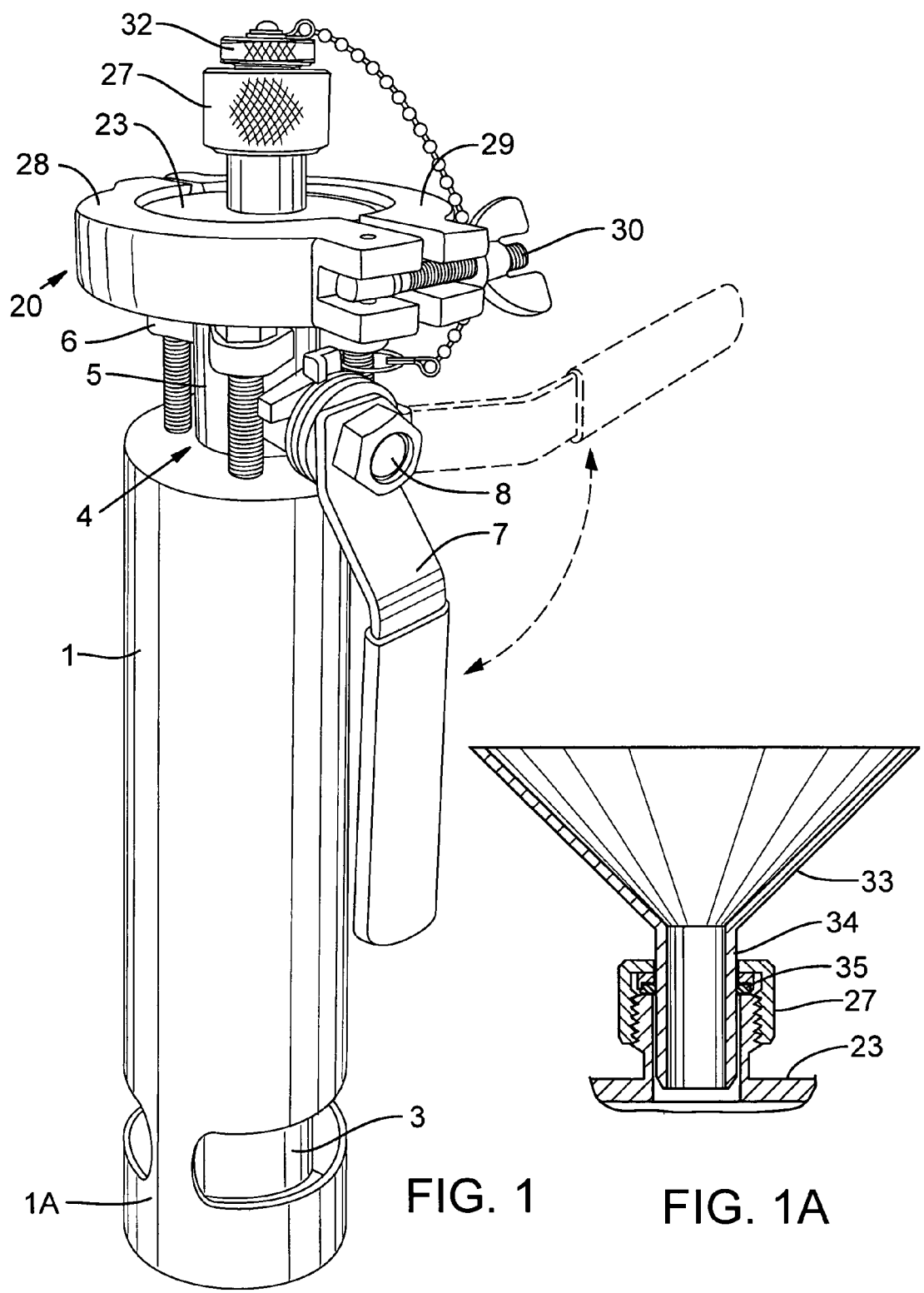
FIG. 1 is a downward perspective of the receptacle.
FIG. 1A is an elevational view of a fragment of the receptacle upper end fitted with a funnel shaped collector.

With continuing attention to the drawings, and particularly FIG. 1, a main tubular body of the portable receptacle is indicated at 1. An open ended extension 1A of the main body houses a vacuum gauge 3 to indicate the vacuumized state of main body 1 prior to use. A top wall of the receptacle has an opening 2.

A valve component 4 of the receptacle includes a valve body 5 with an end plate at 6. A valve handle 7 actuates a shaft 8 which terminates in engagement with a positionable valve member 10 per FIG. 2.

Valve member 10 is plated at 11 to provide an outermost working surface of noble metal, preferably gold as at 11, by the process of electroplating or other suitable plating technique. A suitable plating thickness is of 0.00010 inches while thicker or lesser plating may be utilized and is somewhat determined by the anticipated frequency of receptacle use and cost of manufacture. While other noble metals such as silver or platinum may be suitable for plating of member 10, gold is preferred for its resistance to corrosion and ductility. Further, gold is believed less susceptible to flaking. The surface defining a ball member passageway 13 may be plated and is preferably of at least 0.6250 inches in diameter to permit retrieval of collected particles therethrough.

A suitable material for the valve seats 12 is sold under the trademark Teflon® (a registered trademark of E. I. du Pont de Nemours and Company know as DuPont. Teflon is a synthetic flouropolymer referring to any of the group consisting of Polytetrafluoroethylene, Perfluoroalkoxy. and Fluorinated ethylene propylene. The seats may be of the biased type. The seat material is may, in some instances, be further identified by a suffix PTFE 7C. A valve passageway is at 14.

To reduce the chance of accidental opening of valve 4, it is desirable that handle 7 be parallel to main body 1, when the valve is closed with raising of the handle to the broken line position of FIG. 1 opening the valve.

Figure 2:
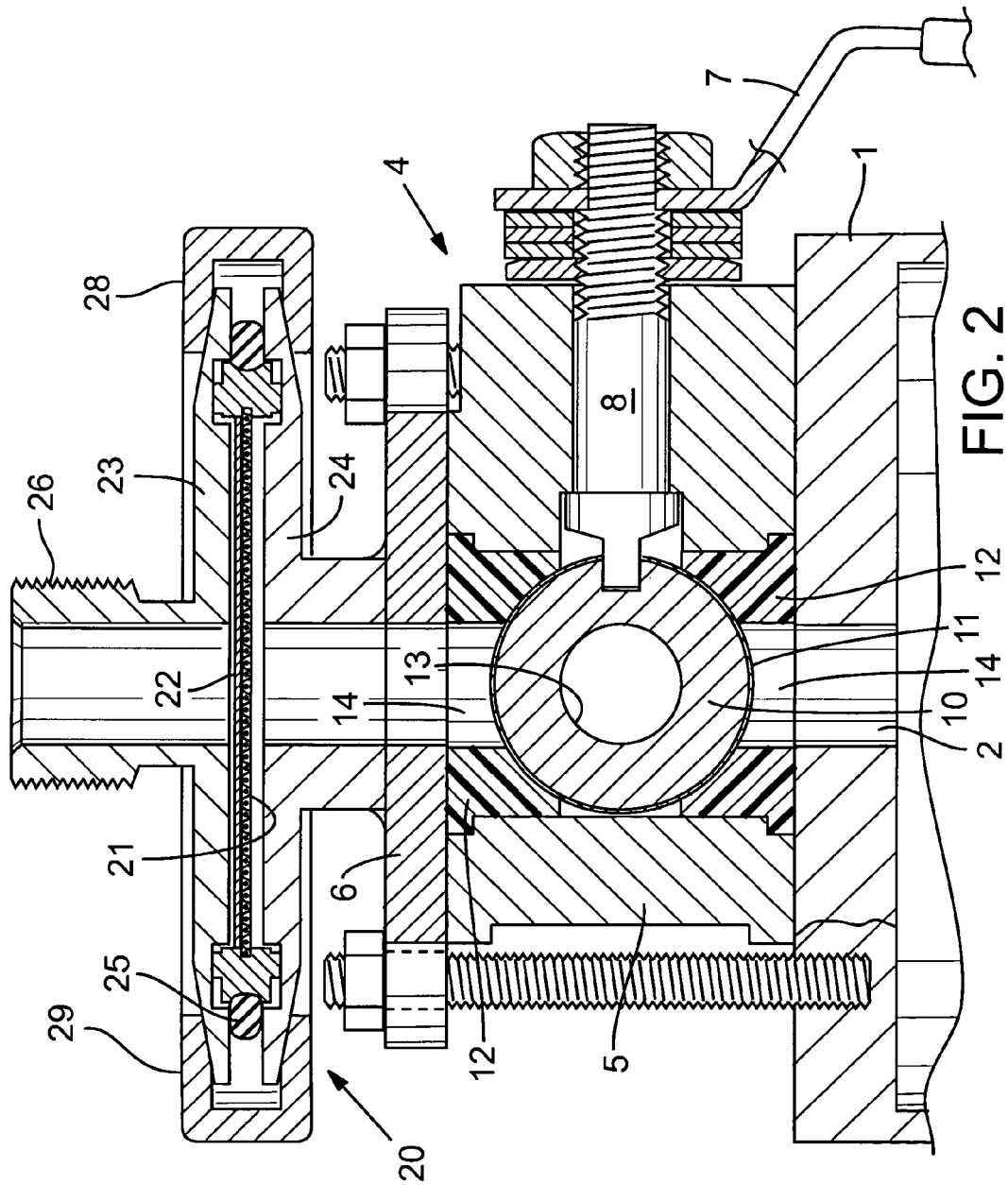
FIG. 2 is a sectional view of the uppermost portion of the receptacle.
Figure 3:
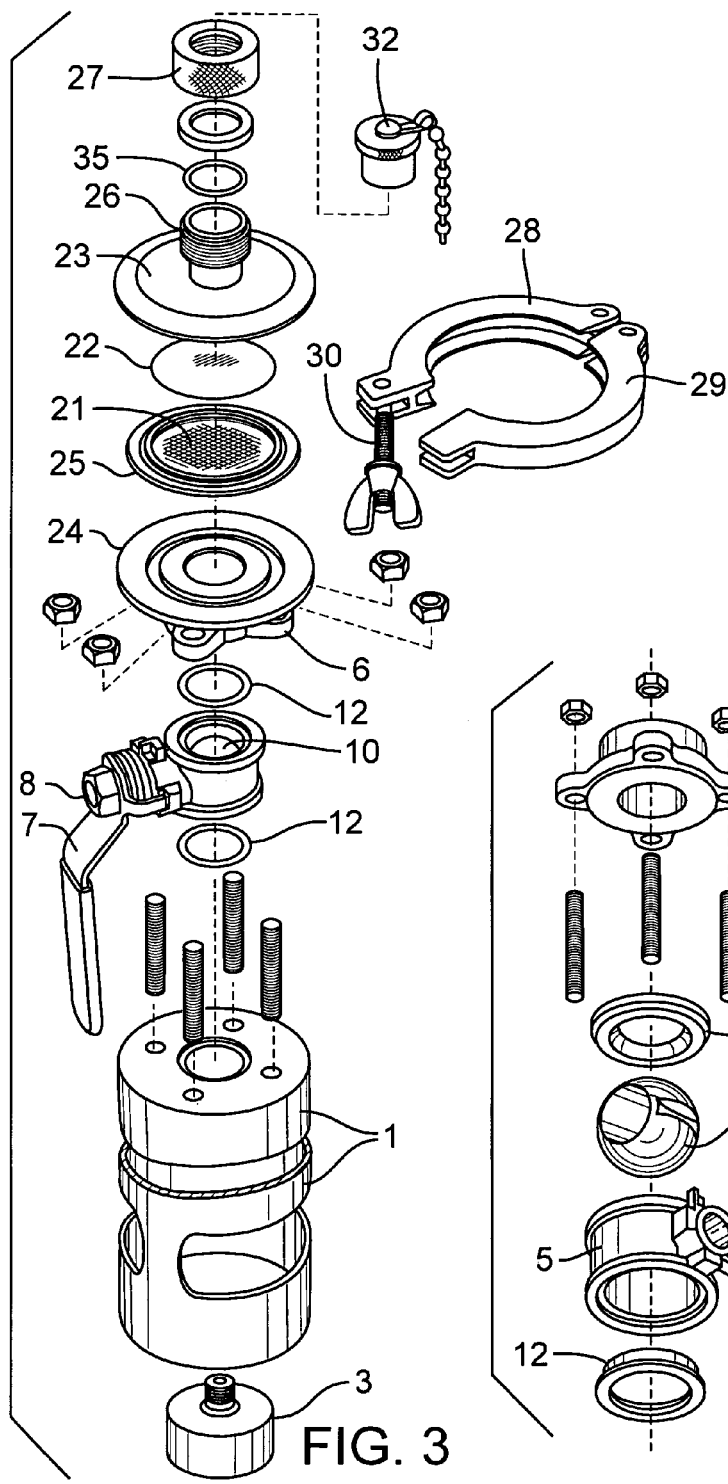
FIG. 3 is an exploded view of the receptacle.
Figure 4:
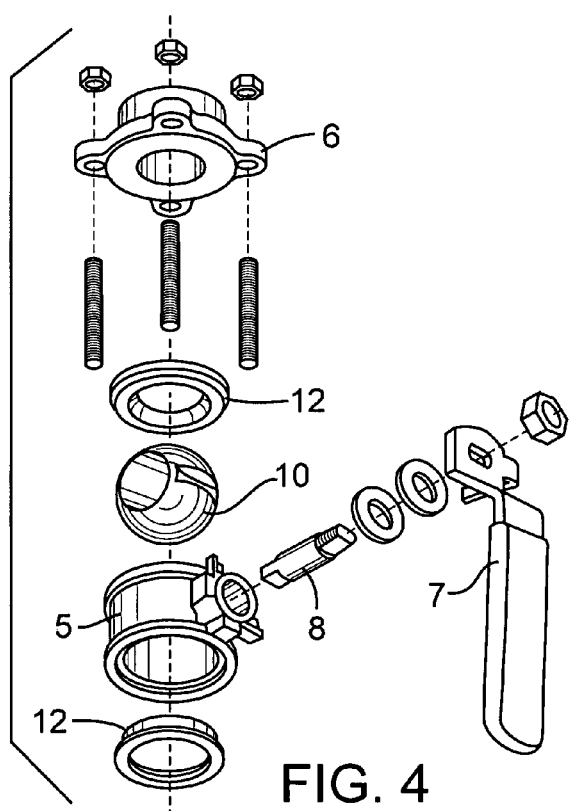
FIG. 4 is an exploded view of a valve assembly of the receptacle.

Continuing with a general description of the receptacle, a filter assembly is generally at 20 and includes plates 23 and 24 as viewed in FIG. 2. The plates jointly confine a fine mesh screen 21 preferably with a fabric component 22 thereon. A clamp with hinged members 28-29 and a locking screw 30 bias the plates closed. An 0-ring 25 seals the plate defined area. Uppermost plate 23 carries a pipe segment 26 threaded to receive a cap 27 (FIG. 3). A plug 32 closes the cap upper end to prevent the entry of foreign matter into the receptacle during storage of the receptacle. An 0-ring 35 is biased upon tightening of cap 27 to close about the neck of a later described collector.

For use of the receptacle without filter assembly 20, clamp 28-29 is released by opening the clamp and removal of upper plate 23 along with filter 21-22.

In FIG. 1A a collector 33 is shown which facilitates the intake of particles from a surface or airborne at a site of an explosion or gas leak producing particulate. The collector is of funnel shape having a neck 34 for insertion into the cap 27 upon plug removal prior to valve opening.

Use of the receptacle is believed apparent from the foregoing description. Prior to storage of the receptacle at and emergency response facility, the same is evacuated to 30 inches Hg and valve 4 is closed. Accordingly, samples of hazardous or explosive agents may be taken for chemical analysis as well as samples of ambient air at illegal drug laboratories and stored for purposes of evidence.

While I have shown but one embodiment of the invention, it will be apparent to those skilled in the art that the invention may be embodied still otherwise without departing from the spirit and scope of the claimed invention.

I claim:

1. In a vacuumized vessel, the improvement comprising:
a valve including a positionable ball member mounted within the valve to rotate from an opened to a closed position, the ball member having an external coating of a noble metal and non-metallic seats that sealingly cooperate with the external coating when the ball member is in the closed position.

2. The improvement claimed in claim 1 wherein the noble metal is gold.

3. The portable vacuumized receptacle as defined in claim 1 wherein the flouropolymer valve seat is a flouropolymer selected from a group consisting of Polytetrafluoroethylene; Perfiuoroalkoxy; and Fluorinated ethylene propylene.

4. A receptacle for vacuumizing for subsequent collection of a sample of air or a gas for purposes of evaluation and comprising:
a portable main body defining a chamber,
a valve assembly on said portable main body including a control for admitting ambient air or a gas into the chamber, a valve member alternately positionable in a first and a second position, having an outermost surface of a noble metal configured to cooperate with a synthetic fluoropolymer seat to effect a seal thereby to maintain the receptacle in a vacuumized state when stored for a lengthy duration prior to the collection of a sample, and
a filter assembly on said valve assembly in communication with an inlet serving said chamber, and including a filter element on which airborne particulate of the sample may be collected.

5. The receptacle claimed in claim 4 wherein the noble metal is gold.

6. The receptacle claimed in claim 4 wherein the valve member is spherical.

7. A portable vacuumized receptacle having a reservoir and comprising:
a valve having a ball member moveable from a first to a second position, the first position opening a valve passageway to communicate the reservoir with the ambient, the ball member having an exterior outermost surface of a noble metal, the ball member being configured to cooperate with a synthetic flouropolymer seat to effect a seal isolating the reservoir from the ambient in the second position.

8. The improvement claimed in claim 7 wherein the noble metal is gold.

9. The portable vacuumized receptacle claimed in claim 7 additionally including a filter assembly in operative communication with the valve passageway of the valve.

10. The filter assembly of claim 9, wherein the filter assembly includes a wire mesh screen, a fabric member, plates confining the wire mesh screen and the fabric member, and a clamp biasing the plates closed.

11. A valve having a movable ball element comprising,
a control coupled to the ball element; and
a synthetic flouropolymer valve seat biased into sealing contact with the ball element, the ball element having a noble metal external outermost surface.

12. The improvement claimed in claim 11 wherein the noble metal is gold.

13. The improvement claimed in claim 11 wherein the noble metal is silver.

14. The improvement claimed in claim 11 wherein the noble metal is platinum.

15. The improvement claimed in claim 11 wherein the noble metal is of a thickness of approximately .00010 inches.

16. The valve as defined in claim 11 wherein the flouropolymer valve seat is a flouropolymer selected from a group consisting of Polytetrafluoroethylene; Perfluoroalkoxy; and Fluorinated ethylene propylene.

17. The valve as defined in claim 11 wherein the flouropolymer valve seat is a flouropolymer selected from a group consisting of Polytetrafluoroethylene; Perfluoroalkoxy; Fluorinated ethylene propylene.

18. A valve for selectably containing a vacuum, the valve comprising:
a synthetic flouropolymer valve seat; and
a valve member to sealingly cooperating with the synthetic flouropolymer valve seat having a valve passageway, said valve member including an outermost surface of noble metal.

19. The valve as defined in claim 18 wherein the flouropolymer valve seat is a flouropolymer selected from a group consisting of Polytetrafluoroethylene; Perfluoroalkoxy; and Fluorinated ethylene propylene.

* * * * *

UNITED STATES PATENT AND TRADEMARK OFFICE
CERTIFICATE OF CORRECTION

| | | |
|---|---|---|
| PATENT NO. | : 7,350,536 B2 | Page 1 of 1 |
| APPLICATION NO. | : 11/249962 | |
| DATED | : April 1, 2008 | |
| INVENTOR(S) | : Robert W. Evans | |

It is certified that error appears in the above-identified patent and that said Letters Patent is hereby corrected as shown below:

In column 1, line 15 add a comma between "explosion" and "chemical".

In column 2, line 35 remove the period between "Perfluoroalkoxy" and "and".

In column 2, line 37 remove the word "is" from between "material" and "may".

Signed and Sealed this

Twenty-eighth Day of October, 2008

JON W. DUDAS
*Director of the United States Patent and Trademark Office*